US011903952B2

(12) United States Patent
Lu et al.

(10) Patent No.: US 11,903,952 B2
(45) Date of Patent: Feb. 20, 2024

(54) VITAMIN D AS AN IMMUNE MODULATOR TO PREVENT IMMUNE-RELATED COMPLICATION FROM COVID-19 INFECTION

(71) Applicants: NORTHWESTERN UNIVERSITY, Evanston, IL (US); Case Western Reserve University, Cleveland, OH (US); The Regents of the University of Colorado, Denver, CO (US)

(72) Inventors: Kurt Q. Lu, Chicago, IL (US); Livia A. Veress, Denver, CO (US); Kevin D. Cooper, Moreland Hills, OH (US); Amisha Wallia, Chicago, IL (US)

(73) Assignees: Northwestern University, Evanston, IL (US); Case Western Reserve University, Cleveland, OH (US); The Regents of the University of Colorado, Denver, CO (US)

( * ) Notice: Subject to any disclaimer, the term of this patent is extended or adjusted under 35 U.S.C. 154(b) by 45 days.

(21) Appl. No.: 17/303,330

(22) Filed: May 26, 2021

(65) Prior Publication Data

US 2021/0369741 A1    Dec. 2, 2021

Related U.S. Application Data

(60) Provisional application No. 63/030,786, filed on May 27, 2020.

(51) Int. Cl.
| | | |
|---|---|---|
| A61K 31/593 | (2006.01) | |
| A61K 45/06 | (2006.01) | |
| A61P 31/14 | (2006.01) | |
| A61P 11/00 | (2006.01) | |
| A61K 31/585 | (2006.01) | |

(52) U.S. Cl.
CPC .......... *A61K 31/593* (2013.01); *A61K 31/585* (2013.01); *A61K 45/06* (2013.01); *A61P 11/00* (2018.01); *A61P 31/14* (2018.01)

(58) Field of Classification Search
CPC .................................................. A61K 31/593
See application file for complete search history.

(56) References Cited

U.S. PATENT DOCUMENTS

| | | | |
|---|---|---|---|
| 4,851,401 A | 7/1989 | DeLuca et al. | |
| 4,857,518 A | 8/1989 | DeLuca et al. | |
| 5,120,722 A | 6/1992 | Baggiolini et al. | |
| 5,237,110 A | 8/1993 | DeLuca et al. | |
| 5,401,731 A * | 3/1995 | Calverley | C07C 401/00 552/653 |
| 5,411,949 A | 5/1995 | Neef et al. | |
| 5,446,035 A | 8/1995 | Neef et al. | |
| 2012/0077786 A1* | 3/2012 | Byron | A61K 31/203 514/167 |
| 2019/0183908 A1 | 6/2019 | Lu | |

FOREIGN PATENT DOCUMENTS

| | | | |
|---|---|---|---|
| WO | 2008115531 A1 | | 9/2008 |
| WO | WO2008115531 | * | 9/2008 |

OTHER PUBLICATIONS

Barut et al. Clin Invest Med, 2016, 39(1): E15-24(abstract).*
Au et al., "Suppression of Hyperactive Immune Responses Protects against Nitrogen Mustard Injury". J Invest Dermatol. 135(12); 2971-81 (2015).
Barut et al. "Reduction of Acute Lung Injury by Administration of Spironolactone After Intestinal Ischemia and Reperfusion in Rats". Clin Invest Med, 2016, 39(1): E15-24(abstract).
Di Rosa et al., "Immuno-modulatory effects of vitamin D3 in human monocyte and macrophages". Cellular Immunology, 280(1):36-43 (2012).
Giovannucci et al., "Prospective Study of Predictors of Vitamin D Status and Cancer Incidence and Mortality in Men". J. Natl. Cancer Institute 98(7):451-9 (2006).
Goss, C. H., et al. "Incidence of acute lung injury in the United States." Critical care medicine 31(6): 1607-1611 (2003).
Iu et al., "Toll-Like Receptor Triggering of a Vitamin D-Mediated Human Antimicrobial Response". Science, 311 (5768): 1770-3 (2006).
Martins et al. "Prevalence of Cardiovascular Risk Factors and the Serum Levels of 25-Hydroxyvitamin D in the United States". Archives of internal medicine 167(11): 1159-65 (2007).
P. Heinrich Stahl, Camille G. Wermuth (Eds.), Handbook of Pharmaceutical Salts Properties, Selection, and Use; 2002.
Zhang et al., "Vitamin D Inhibits Monocyte/macrophage Pro-inflammatory Cytokine Production by Targeting Mitogen- Activated Protein Kinase Phosphatase 1". J. of Immunol., 188(5): 2127-35 (2012).
Rosen, CJ, "Vitamin D Insufficiency". N Engl J Med. 364(3):248-54 (2011).
Sanders et al., "Annual High-Dose Oral Vitamin D and Falls and Fractures in Older Women: A Randomized Controlled Trial". JAMA, 303(18): 1815-22 (2010).
Tian et al., "Pulmonary Pathology of Early-Phase 2019 Novel Coronavirus (COVID-19) Pneumonia in Two Patients With Lung Cancer". Journal of Thoracic Oncology, 15(5): 700-704, (2020).
Wobke et al., "Vitamin D in inflammatory diseases". Frontiers in physiology, 5(244) (2014).
Ku et al., "Pathological findings of COVID-19 associated with acute respiratory distress syndrome". The Lancet, 8(4); 420-422, Apr. 2020.

(Continued)

*Primary Examiner* — Rei Tsang Shiao
(74) *Attorney, Agent, or Firm* — Quarles & Brady LLP

(57) ABSTRACT

Disclosed herein are methods and compositions useful in reducing inflammation, reducing inflammatory exudates, enhancing epithelial tissue generation or regeneration, and/or reducing mean pulmonary artery pressure in the lungs of a subject in need thereof. In particular, the compositions comprise vitamin D, an analog, or metabolite thereof, and the methods include administering the composition to a subject in need thereof. In some embodiments, the subject is suffering from an infection, such as a viral infection, which affects the lungs. In some embodiments, the viral infection comprises SARS-CoV-2.

12 Claims, 6 Drawing Sheets

(56) References Cited

OTHER PUBLICATIONS

Lu, K. Translation of novel and repurposed drugs to address the acute and late effects of mustard exposure. Grantome webpage. Accessed on Mar. 23, 2022. Available online at http://web.archive.org/web/20220323201849/ https://grantome.com/grant/NIH/U01-AR071168-03.

National Institutes of Health. Clinical Trials webpage for NTC02968446. Effect of Vitamin D After Application with Valchlor. Last Update Posted Dec. 23, 2021. Accessed on Mar. 23, 2022. Available online at https://web.archive.org/web/20210408024450/https://clinicaltrials.gov/ct2/show/NCT02968446.

* cited by examiner

VITAMIN D AS AN IMMUNE MODULATOR TO PREVENT IMMUNE-RELATED COMPLICATION FROM COVID-19 INFECTION

CROSS-REFERENCE TO RELATED APPLICATIONS

This application claims the benefit of U.S. Application No. 63/030,786, filed on May 27, 2020, the entire content of which is incorporated herein by reference in its entirety.

BACKGROUND

Vitamin D is primarily known as a supplement. However, when provided in significantly high doses with a strategic regimen, it becomes an intervention that can help prevent and treat inflammation. For symptomatic COVID19 patients, the progression of symptoms from fever and body aches to worsening shortness of breath and multi-organ failure is a hallmark feature of immune activation and inflammation. By correcting this immune dysregulation, COVID-related symptoms can be reduced, and ultimately, disease severity, and potentially the need for mechanical ventilation, ICU admission, and death can also be reduced or eliminated.

SUMMARY

Disclosed herein are methods and compositions useful in reducing inflammation, reducing inflammatory exudates, enhancing epithelial tissue generation or regeneration, and/or reducing mean pulmonary artery pressure in the lungs of a subject in need thereof. In particular, the compositions comprise vitamin D, an analog, or metabolite thereof, and the methods include administering the composition to a subject in need thereof. In some embodiments, the subject is suffering from an infection, such as a viral infection, which affects the lungs. In some embodiments, the viral infection comprises SARS-CoV-2.

DETAILED DESCRIPTION

Figure 1:
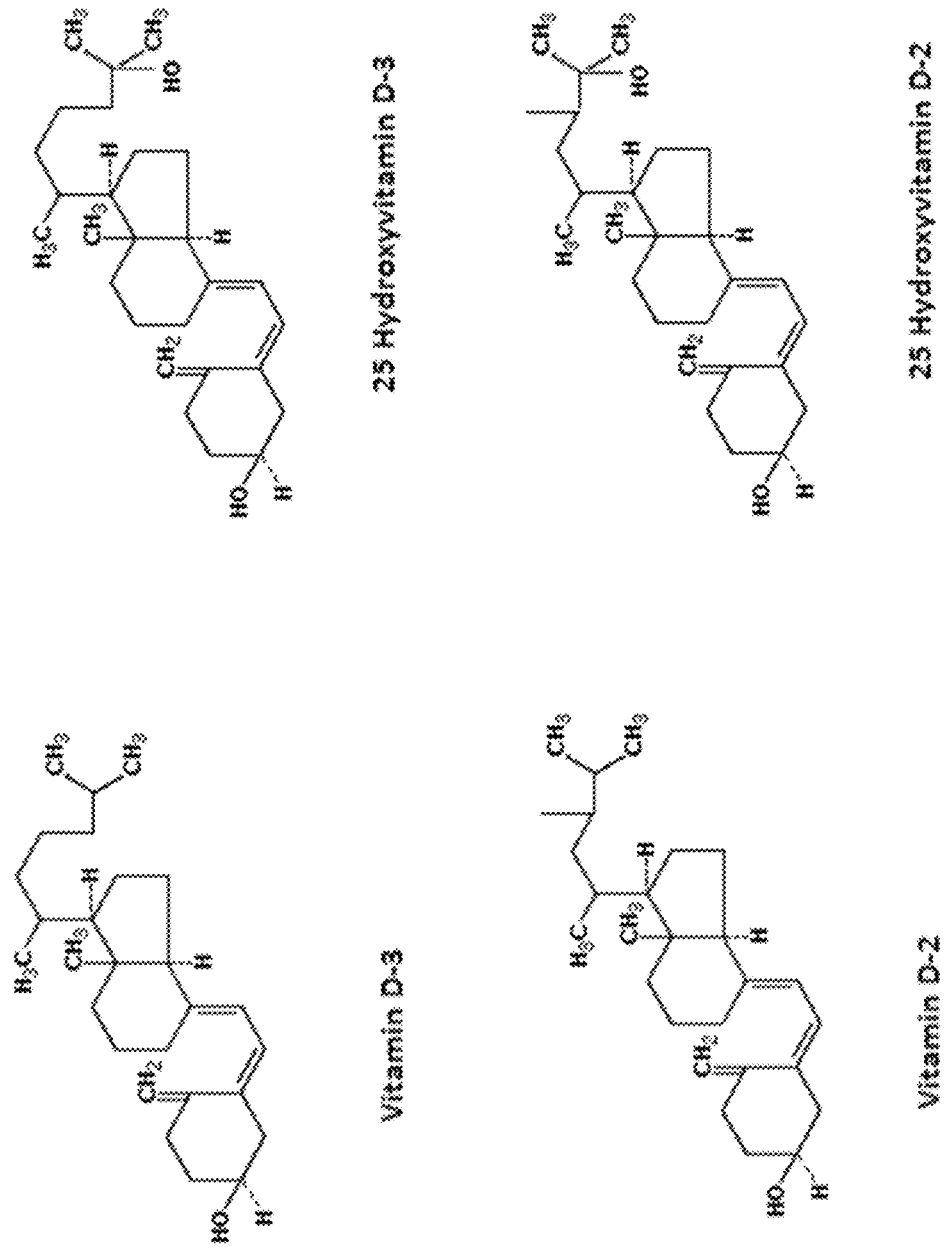
FIG. 1 shows the structure of vitamin D3, 25-hydroxyvitamin D3, vitamin D2, and 25-hydroxyvitamin D2.

The present invention is described herein using several definitions, as set forth below and throughout the application.

As used in this specification and the claims, the singular forms "a," "an," and "the" include plural forms unless the context clearly dictates otherwise. For example, the term "a polypeptide fragment" should be interpreted to mean "one or more a polypeptide fragment" unless the context clearly dictates otherwise. As used herein, the term "plurality" means "two or more."

As used herein, "about," "approximately," "substantially," and "significantly" will be understood by persons of ordinary skill in the art and will vary to some extent on the context in which they are used. If there are uses of the term which are not clear to persons of ordinary skill in the art given the context in which it is used, "about" and "approximately" will mean up to plus or minus 10% of the particular term and "substantially" and "significantly" will mean more than plus or minus 10% of the particular term.

As used herein, the terms "include" and "including" have the same meaning as the terms "comprise" and "comprising." The terms "comprise" and "comprising" should be interpreted as being "open" transitional terms that permit the inclusion of additional components further to those components recited in the claims. The terms "consist" and "consisting of" should be interpreted as being "closed" transitional terms that do not permit the inclusion of additional components other than the components recited in the claims. The term "consisting essentially of" should be interpreted to be partially closed and allowing the inclusion only of additional components that do not fundamentally alter the nature of the claimed subject matter.

As used herein, the term "subject" may be used interchangeably with the term "patient" or "individual" and may include an "animal" and in particular a "mammal." Mammalian subjects may include humans and other primates, domestic animals, farm animals, and companion animals such as dogs, cats, guinea pigs, rabbits, rats, mice, horses, cattle, cows, and the like.

The disclosed methods and compositions may be utilized to treat a subject in need thereof. A "subject in need thereof" is intended to include a subject having or at risk for developing inflammation and/or an inflammatory response, such as in response to an infection that negatively affects the lungs. By way of example, a subject in need thereof may be a subject diagnosed with, at risk for, or likely to be infected with a virus such as SARS CoV-2.

As used herein, the terms "treat" or "treatment" encompass both "preventative" and "curative" treatment. "Preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition. Thus, treatment includes ameliorating or preventing the worsening of existing disease symptoms, preventing additional symptoms from occurring, ameliorating or preventing the underlying systemic causes of symptoms, inhibiting the disorder or disease, e.g., arresting the development of the disorder or disease, relieving the disorder or disease, causing regression of the disorder or disease, relieving a condition caused by the disease or disorder, or stopping the symptoms of the disease or disorder.

Vitamin D

Disclosed herein are compositions and methods useful for the treatment of inflammation, inflammatory conditions, and to arrest an inflammatory response. In particular, the compositions and methods include vitamin D, analogs thereof, or metabolites thereof.

Humans acquire vitamin D from dietary sources and from the UV light-dependent conversion of 7-dehydroxcholesterol to vitamin D3. Vitamin D3 (also known as cholecalciferol) and vitamin D2 (also known as ergocalciferol) are collectively referred to as "vitamin D" and are fat-soluble precursors to the active form of vitamin D, 1,25-dihydroxyvitamin D. The structures of vitamin D2 and vitamin D3 are show in FIG. 1.

Figure 2:
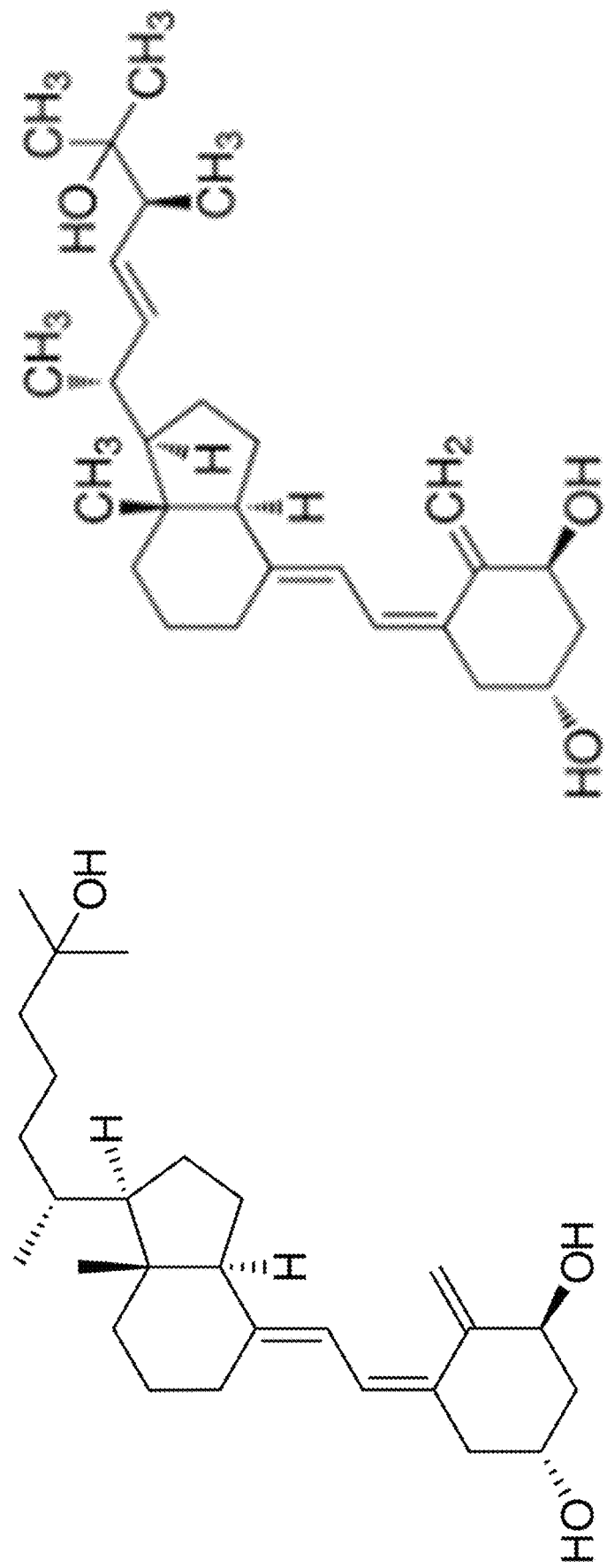
FIG. 2 shows the structure of calcitriol.
Figure 3:
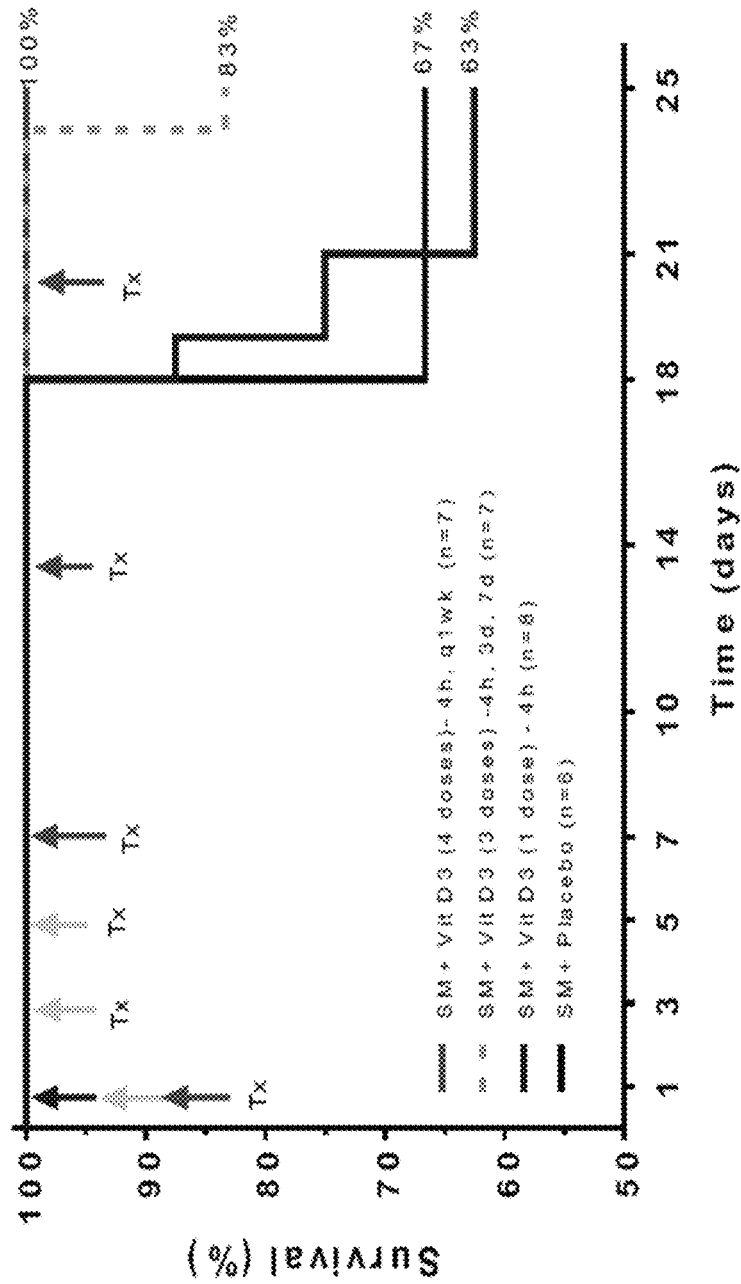
FIG. 3 is a graph showing survival time in days (X-axis) and % survival (Y-axis) for mice treated with various vitamin D regimens after exposure to sulfur mustard (SM). 100% survival: SM+Vit D3 (4 doses); 83% survival: SM+Vit D3 (3 doses); 63% survival: SM+Vit D3 (1 dose); and 67% survival: SM+Placebo.
Figure 4:
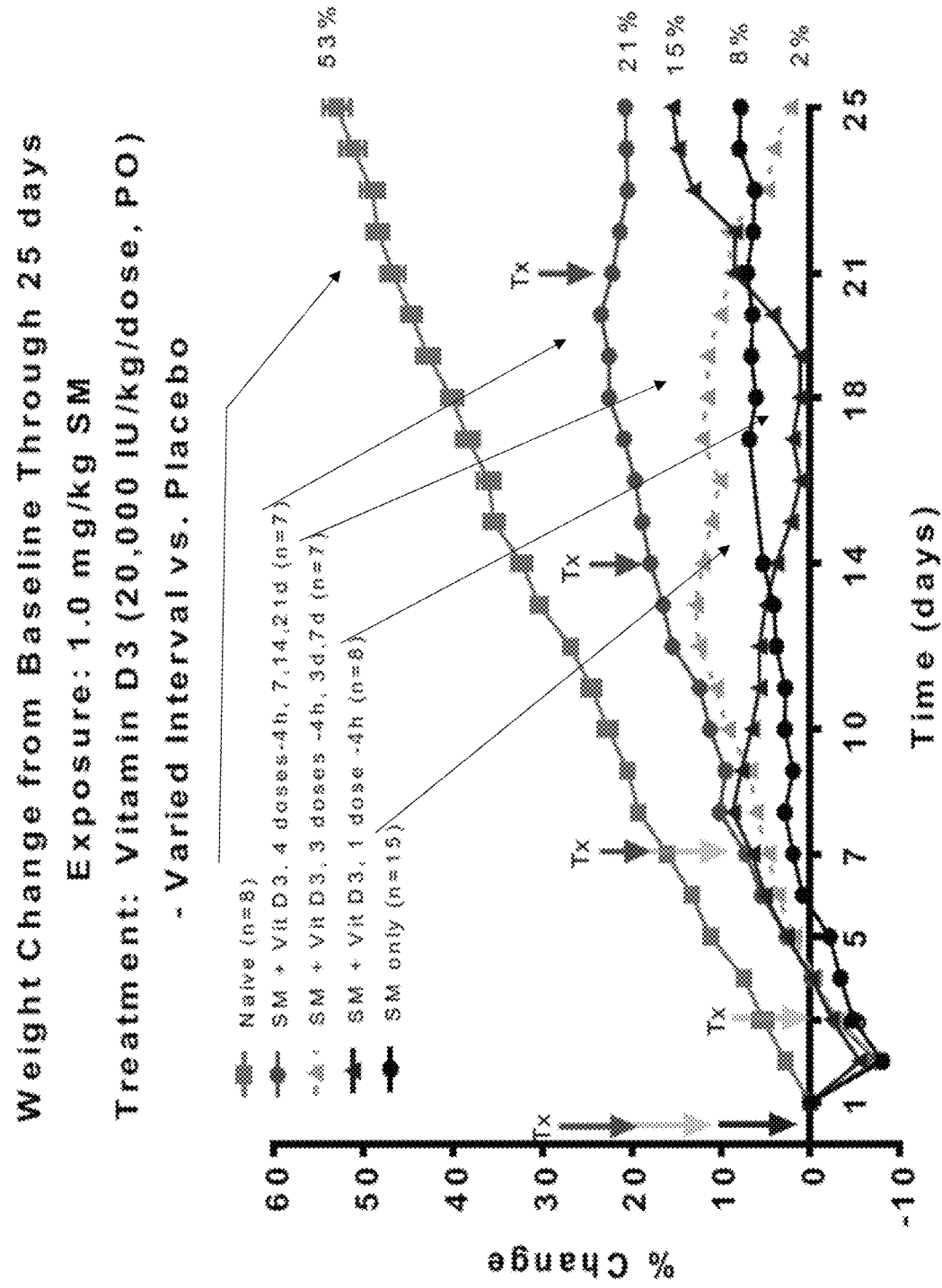
FIG. 4 is a graph showing % weight change (Y-axis) over time (X-axis) for mice treated with various vitamin D regimens after exposure to sulfur mustard (SM).
Figure 5:
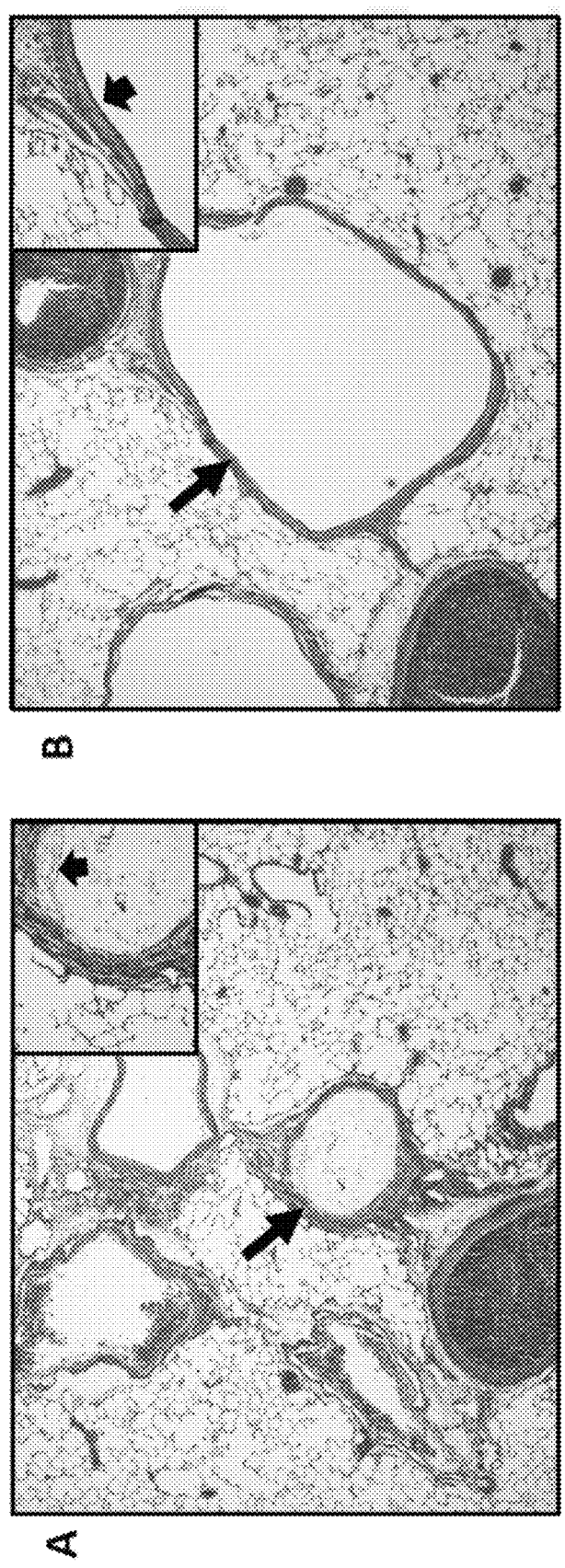
FIG. 5 shows representative pictographs of distal left lung sections of rats 25 days after Sulfur Mustard (SM) inhalation induced lung injury, with and without oral Vitamin D treatment regimen. (A) SM+placebo (oral) treatment at 4 h after exposure, shows severe thickening and constriction of the main bronchial airway (long arrow), with severe luminal inflammatory exudate, and absence of luminal epithelial cell layer (see insert, short arrow). (B) SM+Vitamin D (20,000 IU/kg/dose) given at 4 hours, then at 7, 14 and 21 days after exposure, shows minimal thickening of the main bronchial airway (long arrow), with none to scant luminal exudate, and a continuous luminal epithelial cell layer (see insert, short arrow). Masson Trichrome, 4× magnification (inserts 20×); representative images of n=4-8/group.
Figure 6:
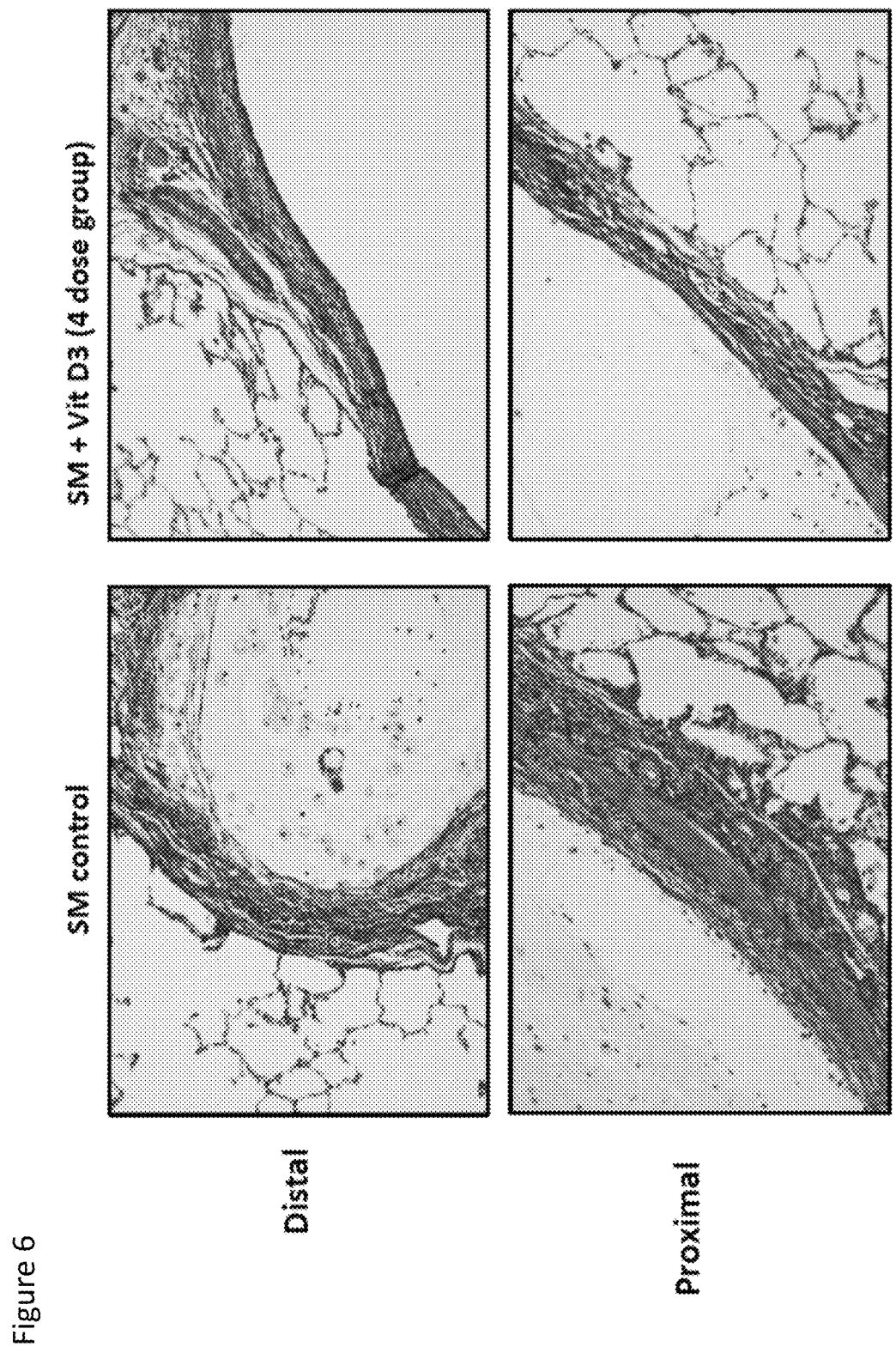
FIG. 6 is a set of representative pictographs of distal left lung sections, proximal large airway as well as distal medium sized airway, of rats 25 day after Sulfur Mustard (SM) inhalation-induced lung injury, with and without oral Vitamin D treatment regimen. In SM controls, severe wall thickening with severe luminal inflammatory exudate is seen in both proximal and distal airways, and a complete absence of luminal epithelial cell layer. In contrast, Vitamin D treated animals (4 doses) had intact airway epithelial barrier, decreased wall thickening, and greatly decreased inflammatory exudate. Masson Trichrome, 20× magnification; representative images of n=4-8/group.

Metabolism of vitamin D3 and vitamin D2 occurs primarily in the liver to produce the vitamin D prohormones 25-hydroxyvitamin D3 and 25-hydroxyvitamin D2, respectively (collectively referred to herein as "25-hydroxyvitamin D," FIG. 1). Further metabolic processing of 25-hydroxyvitamin D occurs mainly in the kidneys by a cytochrome P450 enzyme, CYP27B. CYP27B is also expressed in many extra-renal vitamin D target tissues and can effect local activation of 25-hydroxyvitamin D to produce autocrine and/or paracrine hormonal responses. Specifically, 25-hydroxyvitamin D3 is metabolized to the active vitamin D hormones 1,25-dihydroxyvitamin D3 (also known as calcitriol, FIG. 2) and 25-hydroxyvitamin D2 is metabolized to the active hormone 1,25-dihydroxyvitamin D2 (collectively referred to herein as "1,25-dihydroxyvitamin D").

The vitamin D hormones (e.g., 1,25-dihydroxyvitamin D) regulate a variety of cellular processes via interactions with vitamin D receptors (VDR). In particular, the vitamin D hormones regulate blood calcium levels by controlling the absorption of dietary calcium by the small intestine and the reabsorption of calcium by the kidneys. Excessive hormone levels can lead to abnormally elevated urine calcium (hypercalciuria), blood calcium (hypercalcemia) and blood phosphorus (hyperphosphatemia). Vitamin D deficiency, on the other hand, is associated with secondary hyperparathyroidism, parathyroid gland hyperplasia, hypocalcemia, chronic kidney disease (CKD), and metabolic bone diseases such as osteitis fibrosa cystica, osteomalacia, rickets, osteoporosis, and extraskeletal calcification. Vitamin D hormone has been reported to have many diverse "non-classical" biologic effects beyond its "classical" effects on the parathyroid hormone system. Such effects have been reported in connection with cellular proliferation, the immune system and the cardiovascular system, including the renin-angiotensin system, blood pressure, cellular growth and differentiation, anti-fibrosis, red blood cell formation, hair growth, and muscular function.

Catabolism of vitamin D prohormones, hormones, and analogs is accomplished through the action of cytochrome P450 enzymes. The cytochrome P450 enzyme CYP24 catalyzes the first step in the catabolism of various vitamin D compounds. In particular, for example, CYP24 carries out the conversion of 25-hydroxyvitamin $D_3$ to 24,25-dihydroxyvitamin $D_3$ and the conversion of 1,25-dihydroxyvitamin D3 (calcitriol) to 1,24,25-trihydroxyvitamin D3 eventually giving rise to calcitroic acid. CYP24 can also hydroxylate at the 23 position, resulting in the production of the terminal metabolite 1,25-dihydroxyvitamin D3-26,23-lactone. Further processing by Phase II catabolic enzymes ultimately leads to clearance of vitamin D compounds from the body.

As used herein the term "vitamin D metabolite" refers to compounds formed from vitamin D in the body, and include vitamin D3 metabolites such as alfacalcidol (lhydroxycholecalciferol), calcitriol (1α,25-dihydroxycholecalciferol), and dihydrotachysterol. Examples of Vitamin D2 metabolites include 1α,25-dihydroxyvitamin D2 and 1a,24(S)-dihydroxyvitamin D2. Vitamin D metabolites may be chemically synthesized, or may be isolated.

As used herein the term "vitamin D analog" refers to structural analogs of vitamin D, and includes, but is not limited to the compounds found in Table I, below.

TABLE I

Exemplary Vitamin D Analogs

| Name | Structure |
|---|---|
| Paricalcitol (19-nor-1α,25(OH)2D2) | 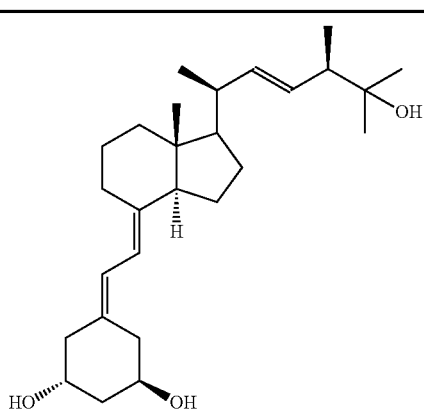 |

TABLE I-continued

Exemplary Vitamin D Analogs

| Name | Structure |
|---|---|
| Doxercalciferol (1α(OH)D2) | 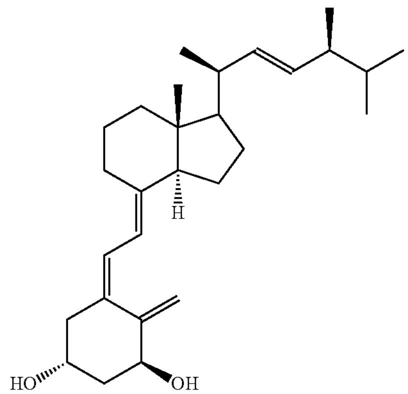 [SMILES: C=C1/C(=C\C=C2/CCC[C@]3(C)C([C@@H](C)/C=C/[C@@H](C)C(C)C)CC[C@@H]23)C[C@@H](O)C[C@@H]1O] |
| Falecalcitriol (26,27 F6-1α,25(OH)2D3) | 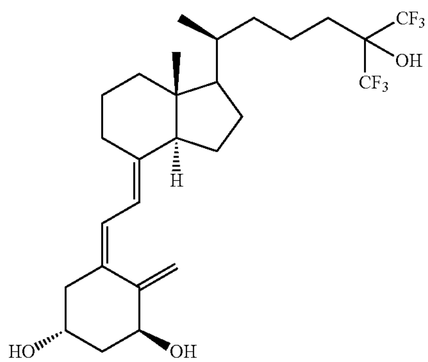 [SMILES: C=C1/C(=C\C=C2/CCC[C@]3(C)C([C@@H](C)CCCC(O)(C(F)(F)F)C(F)(F)F)CC[C@@H]23)C[C@@H](O)C[C@@H]1O] |
| Maxacalcitol (22oxa-1α,25(OH)2D3) | 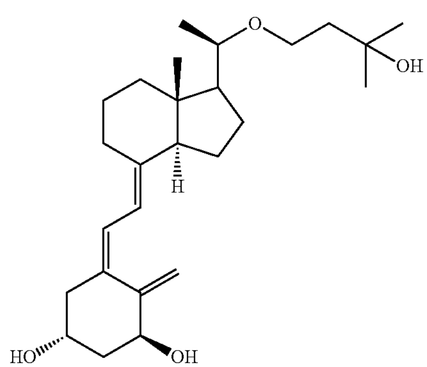 [SMILES: C=C1/C(=C\C=C2/CCC[C@]3(C)C([C@@H](C)OCCC(C)(C)O)CC[C@@H]23)C[C@@H](O)C[C@@H]1O] |
| Tacalcitol (1α,24(R)(OH)2D3) | 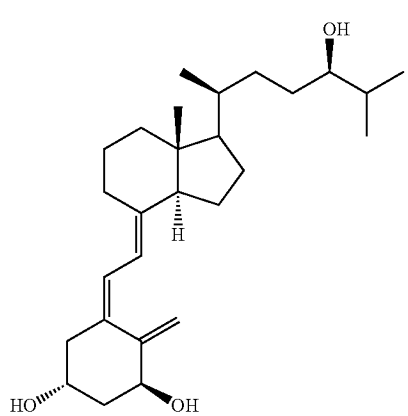 [SMILES: C=C1/C(=C\C=C2/CCC[C@]3(C)C([C@@H](C)CC[C@@H](O)C(C)C)CC[C@@H]23)C[C@@H](O)C[C@@H]1O] |

TABLE I-continued
Exemplary Vitamin D Analogs
| Name | Structure |
|---|---|
| Calcipotriol (22-ene-26,27-dehydro-1α,25(OH)2D3) | 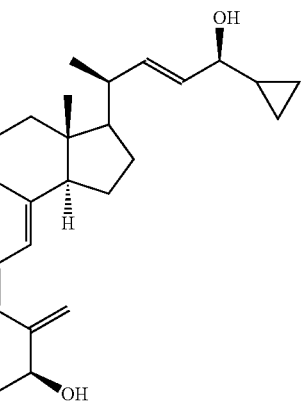 |
| Alfacalcidol (1α(OH)D3) | 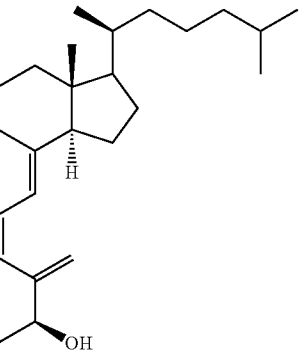 |
| Eldecalcidol (2β-(3-hydroxypropoxy)-1α,25(OH)2D3) | 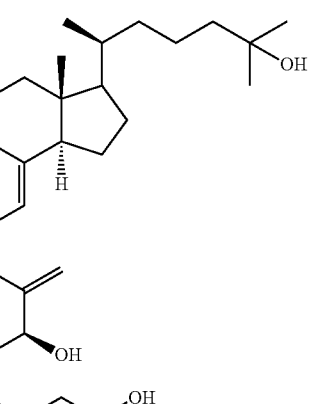 |

TABLE I-continued
Exemplary Vitamin D Analogs
| Name | Structure |
|---|---|
| Seocalcitol (22,24-diene-24,26,27-trishomo-1α,25(OH)2D3) | 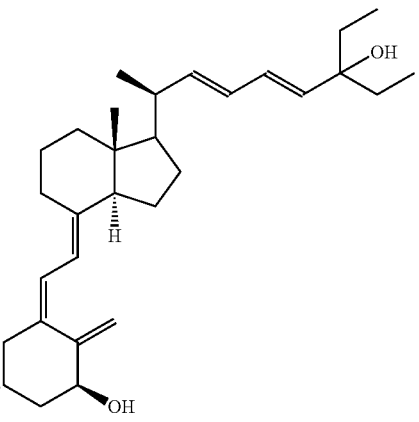 |
| 20-epi-1α,25(OH)2D3 | 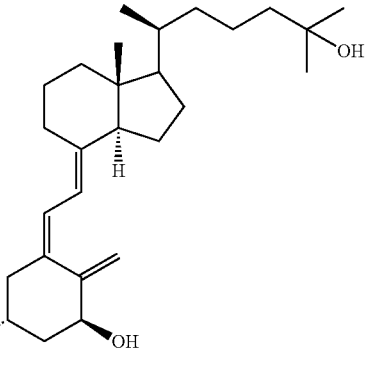 |
| Lexicalcitol (20-epi-22-oxa-24,26,27-trishomo-1α,25(OH)2D3) | 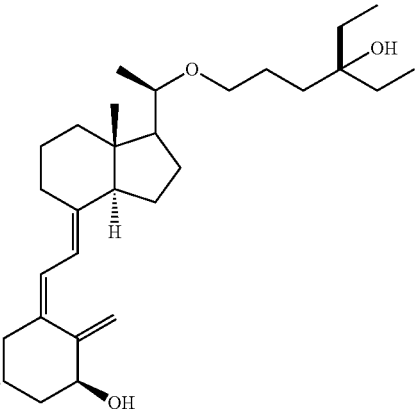 |
| CD578 (17-methyl-19-nor-21-nor-23-yne-26,27-F6-1α,25(OH)2D3) | 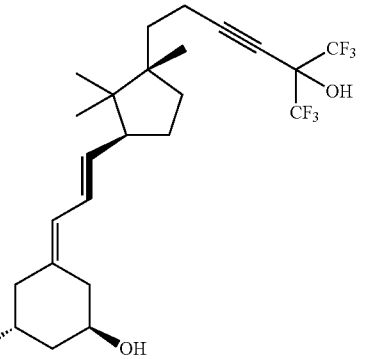 |

TABLE I-continued
Exemplary Vitamin D Analogs
| Name | Structure |
|---|---|
| Inecalcitol (19-nor-14-epi-23-yne-1α,25(OH)2D3) | 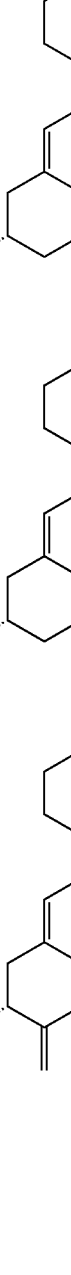 |
| TX527 (19-nor-14,20-bisepi-23-yne-1α,25(OH)2D3) | 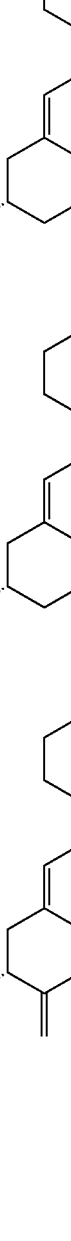 |
| 2MD (2-methylene-19-nor-(20S)-1α,25(OH)2D3) | 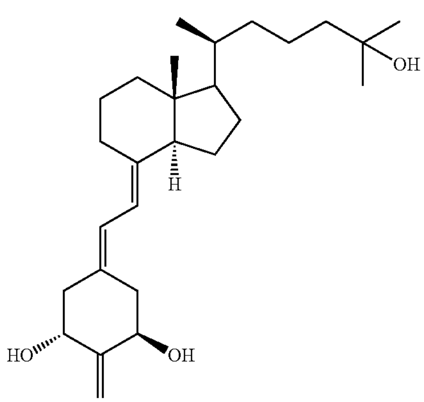 [SMILES: C=C1[C@H](O)CC(=C/C=C2\CCC[C@]3(C)C([C@@H](C)CCCC(C)(C)O)CC[C@@H]23)C[C@H]1O] |
| WY1112 (Seco-C-9,11-bisnor-17-methyl-20-epi-26,27-F6-1α,25(OH)2D3) | 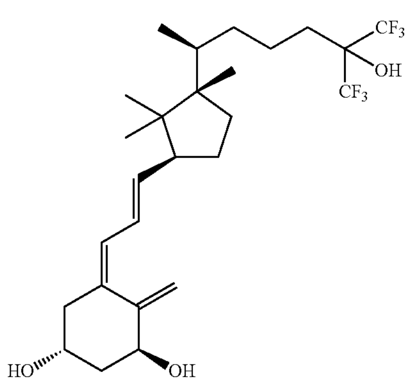 [SMILES: C=C1/C(=C\C=C\[C@@H]2CC[C@@](C)([C@@H](C)CCCC(O)(C(F)(F)F)C(F)(F)F)C2(C)C)C[C@@H](O)C[C@@H]1O] |

TABLE I-continued

Exemplary Vitamin D Analogs

| Name | Structure |
|---|---|
| PRI-2205 ((5E,7E)-22-ene-26,27-dehydro-1α,25(OH)2D3) | 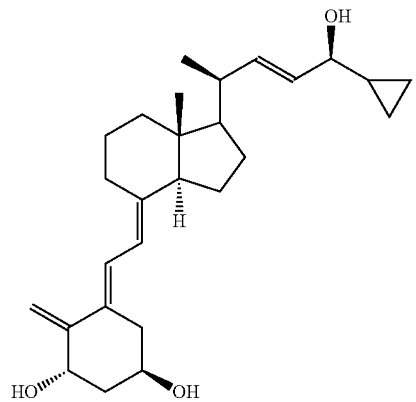 [SMILES: C=C1/C(=C/C=C2\CCC[C@]3(C)C([C@@H](C)/C=C/[C@@H](O)C4CC4)CC[C@@H]23)C[C@@H](O)C[C@@H]1O] |
| ILX23-7553 (16-ene-23-yne-1α,25(OH)2D3) | 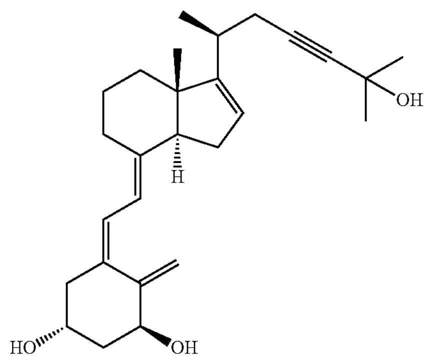 [SMILES: C=C1/C(=C\C=C2/CCC[C@]3(C)C([C@@H](C)CC#CC(C)(C)O)=CC[C@@H]23)C[C@@H](O)C[C@@H]1O] |

Given the large number of vitamin D analogs that have been synthesized to date, presented herein are an exemplary few. It is noted that the analogs presented in Table I in bold font have been clinically approved. Additional vitamin D analogs are described in U.S. Pat. No. 4,851,401 (cyclopentano-vitamin D analogs), U.S. Pat. No. 5,120,722 (trihydroxycalciferol derivatives), U.S. Pat. No. 5,446,035 (20-methyl substituted vitamin D), U.S. Pat. No. 5,411,949 (23-oxa-derivatives), U.S. Pat. No. 5,237,110 (19-nor-vitamin D compounds), U.S. Pat. No. 4,857,518 (hydroxylated 24-homo-vitamin D derivatives).

Typically, the recommended dosage of vitamin D may vary based on the intended use, age, and conditions of the subject. For example, as a nutritional supplement, the recommended daily amount of vitamin D is 400 international units (IU) for children up to age 12 months, 600 IU for ages 1 to 70 years, and 800 IU for people over 70 years. For subjects suffering from osteoporosis, vitamin D dosage may be 800-1000 IU for both prophylaxis and treatment; for subject suffering from hyperthyroidism, vitamin D dosage may be 50,000-200,000 (0.625-5 mg); for subjects suffering from vitamin D-resistant rickets, dosage may be 12,000-500,000 IU (0.3-12.5 mg); for subjects suffering from or at risk of familial hypophosphatemia, vitamin D dosage may be 10,000-60,000 IU (0.25-1.5 mg). With respect to vitamin D. 1 IU=0.025 µg; 40,000 IU=1 mg.

While vitamin D is often administered orally, it can also be administered via numerous other conventional routes, including parenterally and topically. Because it is a well-known and well-studied compound, is typically safe to administer to the general population as well as to "at risk" subjects, such as pediatric, pregnant, geriatric, immune-suppressed, and critically ill subjects.

Investigators have demonstrated that vitamin D plays a role in modulation of immune responses, inflammatory disease, cardiovascular health, and carcinogenesis. Giovannucci et al., J. Natl. Cancer Institute 98(7):451-9 (2006); Martins et al. Archives of internal medicine 167(11): 1159-65 (2007); Rosen, C J, N Engl J Med. 364(3):248-54 (2011); Sanders et al., JAMA, 303(18):1815-22 (2010); Wobke et al., Frontiers in physiology 5:244 (2014). Vitamin D has pleiotropic effects on the immune system, including the enhancement of anti-microbial responses, induction of autophagy, and suppression of pro-inflammatory mediators, including tumor necrosis factor-a (TNF-α). Di Rosa et al., Cellular immunology, 280(1):36-43 (2012); Liu et al., Science, 311 (5768):1770-3 (2006); Zhang et al., J. of Immunol., 188(5): 2127-35 (2012). In addition, it was recently demonstrated that intervention with a single dose of vitamin D is capable of rapidly attenuating an inflammatory response in a mouse model of chemical induced skin injury through inhibition of inducible nitric oxide synthase (iNOS) and TNF-α by activated macrophages. Au et al., J Invest Dermatol. 135(12); 2971-81 (2015). Vitamin D treatment has also been shown to reduce pro-inflammatory mediators such as TNF-α, iNOS, IL-6, COX-2, and MMP9 in the skin when administered at high dosage (e.g., 200,000 IU, orally) after UV exposure or chemical burn (topical nitrogen mustard exposure). Additional anti-inflammatory properties of vitamin D administration, with respect to epidermal and cutaneous healing, are demonstrated in U.S. Patent Appl. No. 2019/0183908, herein incorporated by reference in its entirety.

Compositions

Disclosed herein are compositions comprising one or more active agents, such as vitamin D, vitamin D analogs, and vitamin D metabolites or pharmaceutically acceptable salts thereof. In some embodiments, the active agent comprises one or more of vitamin D2, vitamin D3, 25-hydroxyvitamin D2, 25-hydroxyvitamin D3, 1,25-dihydroxyvitamin D2 and 1,25-dihydroxyvitamin D3 (calcitriol).

As used herein, the term "pharmaceutical composition" describes a composition comprising an active agent, such as vitamin D, an analog thereof, or a metabolite thereof, and in some embodiments, one or more pharmaceutically acceptable excipients. The excipient(s) are acceptable in the sense of being compatible with the other ingredients of the composition and not deleterious to the recipient thereof. In accordance with another aspect of the invention there is also provided a process for the preparation of a pharmaceutical composition including the active agent (e.g., vitamin D), or pharmaceutically acceptable salts thereof, with one or more pharmaceutically acceptable excipients. The pharmaceutical compositions can be used in the treatment and/or prophylaxis of any of the conditions described herein.

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

Used herein, the term "pharmaceutically acceptable salt" refers to pharmaceutically acceptable salts derived from a variety of organic and inorganic counter ions well known in the art and include, by way of example only, sodium, potassium, calcium, magnesium, ammonium, and tetraalkylammonium, and when the molecule contains a basic functionality, salts of organic or inorganic acids, such as hydrochloride, hydrobromide, tartrate, mesylate, acetate, maleate, and oxalate. Suitable salts include those described in P. Heinrich Stahl, Camille G. Wermuth (Eds.), Handbook of Pharmaceutical Salts Properties, Selection, and Use; 2002.

The skilled artisan will appreciate that pharmaceutically acceptable salts of compounds may be prepared. These pharmaceutically acceptable salts may be prepared in situ during the final isolation and purification of the compound, or by separately reacting the purified compound in its free acid or free base form with a suitable base or acid, respectively.

Accordingly, the word "or" in the context of "a compound or a pharmaceutically acceptable salt thereof" is understood to refer to either a compound or a pharmaceutically acceptable salt thereof (alternative), or a compound and a pharmaceutically acceptable salt thereof (in combination).

As used herein, the term "excipient" means the substances used to formulate active pharmaceutical ingredients into pharmaceutical formulations. Excipients (e.g., mannitol, Captisol®, lactose, starch, magnesium stearate, sodium saccharine, talcum, cellulose, sodium croscarmellose, glucose, gelatin, sucrose, magnesium carbonate, and the like) are an integral part of pharmaceutical development and help to achieve the desired product profile including but not limited to an aid in manufacturing, modify a drug's stability, and efficacy. Acceptable excipients are non-toxic and do not adversely affect the therapeutic benefit of at least one chemical entity described herein. Such excipient may be any solid, liquid, semi-solid or, in the case of an aerosol composition, gaseous excipient that is generally available to one of skill in the art. Further the term "excipient" encompasses solubilizing agents, stabilizers, carriers, diluents, bulking agents, pH buffering agents, tonicifying agents, antimicrobial agents, wetting agents, and emulsifying agents (e.g., sodium acetate, sodium citrate, cyclodextrin derivatives, sorbitan monolaurate, triethanolamine acetate, triethanolamine oleate, and the like).

As used herein, "lyophilization," "lyophilized," and "freeze-dried" refer to a process by which the material to be dried is first frozen and then the ice or frozen solvent is removed by sublimation in a vacuum environment. The term "lyophilized powder" or "lyophilized preparation" refers to any solid material obtained by lyophilization, i.e., freeze-drying of an aqueous solution. The aqueous solution may contain non-aqueous solvents, i.e. a solution composed of aqueous and one or more non-aqueous solvent(s). Preferably, a lyophilized preparation is one in which the solid material is obtained by freeze-drying a solution composed of water as a pharmaceutically acceptable excipient.

The pharmaceutical compositions and compounds described herein may be adapted for a variety of administration forms. By way of example, the compositions herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms.

Pharmaceutical compositions disclosed herein may be formulated for administration by any suitable route of delivery, such as oral, parenteral, rectal, nasal, topical, or ocular routes, or by inhalation. For nasal, inhaled, or oral administration, the pharmaceutical compositions may be formulated, for example, as a spray formulation also containing a suitable carrier. The active agents may be formulated for rectal administration as a suppository. Another formulation of the active agents may utilize a patch formulation to effect transdermal delivery.

As noted above, the active agents (e.g., vitamin D, analogs, or metabolites) described herein may be adapted for parental administration and may include aqueous and non-aqueous sterile injection solutions which may contain antioxidants, buffers, bacteriostats and solutes which render the composition isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets. For parenteral use, including intravenous, intramuscular, intraperitoneal, intranasal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampoules or disposable injection devices, in multidose forms such as vials from which the appropriate dose may be withdrawn, or in a solid form or pre-concentrate that can be used to prepare an injectable formulation.

For oral administration, the active agents disclosed herein (e.g., vitamin D, analogs, or metabolites) may be provided in a solid form, such as a tablet or capsule, or as a solution, emulsion, or suspension. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol. Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

Oral dosage packs are also provided herein. In an exemplary oral dose pack, tablets or capsules are provided, each tablet or capsule (or set of tables or capsules), containing a single dose of the active agent (e.g., vitamin D, analog or metabolite thereof). For example, a dose pack of the present technology may include sufficient, pre-packaged dosages for a subject to self-administer 4 doses, 5 doses, 6 doses, 7 doses, 8 doses, 9 doses, or 10 doses or more. In some embodiments, the dose packs include a tapered dosage. By way of example, and not by way of limitation, in some embodiments, a dose pack includes a first dose of 200,000 IU of vitamin D to be taken on day 1; a second dose of 100,000 IU of vitamin D to be taken on day 5; a third dose of 50,000 IU of vitamin D to be taken on day 10; and a fourth dose of 50,000 IU of vitamin D to be taken on day 15. In some embodiments, a dose may comprise multiple tables or capsules, e.g., with each table or capsule comprising 50,000 IU of the active agent. Thus, in the above example, the first dose of 200,000 IU would include 4 tablets or capsules; the second dose of 100,000 IU would include 2 tablets or capsules, and the third and fourth doses of 50,000 IU would each include one tablet or capsule. The dose pack content may be adjusted (prescribed) for each individual patient with respect to the amount of active agent in each dosage, and the timing of each dosage (i.e., when to take each dose).

In some embodiments, therapeutic compositions comprise, in addition to vitamin D an analog or metabolite thereof, one or more additional active agents. In some embodiments, the one or more additional active agents may include an anti-inflammatory agent (e.g., corticosteroids, phosphodiesterase-4 inhibitors), antibiotics, mycophenolate, azathioprine, cyclophosphamide, pirfenidone, nintendanib, bronchodilators, such as $\beta$2-agonists and anticholinergics, mucolytics, antiviral agents, a diuretic such as spironolacatone, and additional autophagy activators such as, but not limited to mTOR pathway inhibitors (e.g., rapamycin), trehalose, loperamide, amiodarone, niguldipine, pimozidine, nicardipine, penitrem A, flusirilene, and trifluoperazine. By way of example, but not by way of limitation, in some embodiments, a pharmaceutical composition comprises vitamin D, an analog thereof, or a metabolite thereof, and at least one diuretic. In some embodiments, the diuretic comprises spironolactone. In some embodiment, the composition comprise, per dose, from about 50 mg to about 400 mg, or about 50 mg, about 75 mg, about 100 mg, about 150 mg, about 200 mg, about 300 mg, or about 400 mg of diuretic (e.g., spironolactone).

In some embodiments, the active agent (e.g., vitamin D, analogs, or metabolites thereof) is formulated to provide, for a 70 kg human subject, between about 100,000 to about 500,000 IU per dose, from about 150,000 IU to about 250,000 IU per dose, or about 200,000 IU per dose. In some embodiments, the composition comprises about 100,000 IU, about 150,000 IU, 200,000 IU, about 250,000 IU, about 300,000 IU, about 350,000 IU, about 400,000 IU, or about 500,000 IU. In some embodiments, the active agent (e.g., vitamin D, analogs or metabolites thereof) is formulated to provide, for a 70 kg human subject, between about 1000 IU to about 100,000 IU per dose, between about, between about 2500 to about 75,000, between about 5000 to about 50,000 IU, between about 10,000 to about 30,000 IU. Dosages can be adjusted according to the weight and/or condition of the subject, or other factors, according to sound medical judgement. In some embodiments, the dosage is tapered over time.

Actual methods of preparing such dosage forms are known, or will be apparent, to those skilled in the art; for example, see Remington's Pharmaceutical Sciences, Mack Publishing Company, Easton, Pa.

Lung Injuries

Disclosed herein are methods and compositions useful in the treatment of lung injuries in a subject in need thereof. In some embodiments, the lung injury exhibits one or more of the following characteristics: thickening and constriction of the bronchial airways (main, proximal, and distal), luminal inflammatory exudates, absence of luminal epithelial cell layers, edema, increased reactive oxygen species (ROS), increased inflammation, an increase in mean pulmonary pressure, and disruption of the alveolar epithelial barrier. In some embodiments, a lung injury is caused by one or more of: acute lung injury; acute respiratory distress syndrome; chronic respiratory distress syndrome, interstitial lung disease; chronic obstructive pulmonary disease (COPD); fibrosis; infection including bacterial and viral infection; asthma; allergies; inhalation of toxic substances and/or smoke; radiation exposure; smoking; cancer; and traumatic injury to the thorax/lung, such as penetrating wounds (e.g., such as with a bullet or a knife).

In some embodiments, the viral infection comprises a respiratory viral infection. By way of example, but not by way of limitation, respiratory viral infections include adenovirus, bocavirus, coronavirus, metapneumovirus, parainfluenza virus, influenza virus, respiratory syncytial virus, and rhinovirus. In some embodiment, the bacterial infection comprises a respiratory bacterial infection. By way of example, but not by way of limitation, bacterial infections include *Streptococcus pneumonia, Haemophilus influenza, Moraxella catarrhalis, Staphylococcus aureus, Mycoplasma*, atypical mycobacteria, and *Streptococcus pyrogens*.

Acute lung injury (ALI) can be a fatal complication of viral infections that affect the lung, such as influenza infections. In particular, the elderly is a population at risk of increase morbidity and mortality from such infections. ALI is characterized by three phases: i) In the exudative phase there is an increase in alveolar-capillary permeability, increase inflammatory markers in the bronchoalveolar lavage fluid (BALF) and impairment of lung compliance. Impairment of the alveolar epithelial barrier by disruption of cell adhesion proteins is an important mechanism during this phase. ii) In the fibroproliferative phase there is increase collagen deposition and lung fibrosis. iii) In the resolution phase, proliferation and differentiation of lung progenitor cells play a role in lung repair mechanisms.

ALI includes Acute Respiratory Distress Syndrome (ARDS) and also milder forms of lung injury. ARDS is a sudden failure of the respiratory system, characterized by widespread inflammation of the lung that leads to fluid leaking into the alveoli, impairing gas exchange. It is associated with pulmonary cytokine release, impaired endothelial barriers, fluid accumulation in distal airspaces, and fibrotic changes. ARDS is considered a clinical syndrome, symptoms of which include hypoxemia, bilateral lung infiltrates, and normal wedge pressure.

The primary causes of ARDS/ALI are sepsis (infection of the bloodstream), inhalation of harmful substances, severe pneumonia, and viral infections that affect the lungs (influenza, MERS, SARS, Ebola, Hunta virus, etc.). The only current treatment of ARDS/ALI is lung protective ventilation. Despite recent improvements in ventilation strategies, ARDS mortality continues to be close to 40%. If ventilation is not successful, a lung transplant is necessary. There are currently no medications that repair lung tissue. Therefore, there is a critical need to develop novel and effective therapies for patients with ALI, and especially in patients with viral-infection-induced ALI.

Viral pneumonias are also a common cause of ALI, with influenza virus being one of the most common viruses responsible for ALI. ALI induced by influenza virus (and likely other viruses such as SARS), share some physiological and biological effects present in other causes of ALI including increase inflammatory lung response, impairment of the alveolar-capillary barrier, and decrease lung compliance. Influenza viral infection increases lung epithelial barrier permeability, disrupt lung epithelial tight junctions, increase reactive oxygen species (ROS) production, activate PKC zeta, and can activate TGFβ, an essential mediator in ALI.

Interstitial lung disease describes a large group of disorders, most of which cause progressive scarring of lung tissue. The scarring associated with interstitial lung disease eventually affects the ability to breathe and get enough oxygen into the bloodstream. Interstitial lung disease can be caused by long-term exposure to hazardous materials, such as asbestos. Some types of autoimmune diseases, such as rheumatoid arthritis, also can cause interstitial lung disease. In some cases, however, the causes remain unknown. Once lung scarring occurs, it is generally irreversible. Medications may slow the damage of interstitial lung disease, but many people never regain full use of their lungs. Lung transplant is an option for some people.

Pulmonary fibrosis is a respiratory disease caused by excess fibrosis connective tissue in the lungs. This excess connective tissue leads to thickening of the walls of the lung, causing reduced oxygen supply in the blood. It is a common secondary effect of interstitial lung disease (a large group of disorders, most of which cause progressive scarring of lung tissue). Current treatments for pulmonary fibrosis aim at preventing the spread of the disease. There are no treatments available that rebuild lung tissue. If the disease is severe, a lung transplant may be needed.

Approximately 250,000 Americans develop ALI annually (Goss, Christopher H., et al. "Incidence of acute lung injury in the United States." Critical care medicine 31.6 (2003): 1607-1611). Approximately 190,000 Americans develop ARDS annually (http://www.lung.org/lung-disease/acute-respiratory-distress-syndrome/understandingards.html). An estimated 132,000 people in the US have pulmonary fibrosis, with many more having some form of interstitial lung disease. All of these diseases harm lung tissue.

Another cause of lung injury is viral infection due to coronavirus, such as SARS-CoV-2. Since December 2019, the outbreak of a novel coronavirus, severe acute respiratory syndrome coronavirus 2 (SARS-CoV-2), infection (coronavirus disease 2019 [COVID-19]) that started in Wuhan, Hubei Province, People's Republic of China, is now a global pandemic. Although patients initially present with fever with or without respiratory symptoms, various degrees of pulmonary abnormalities develop later in all patients, and these are typically observable via chest computed tomography (CT) imaging. Most patients only have a common, mild form of illness, but approximately 15% to 20% fall in the severe group, meaning they require assisted oxygenation as part of treatment. The severe group has a high mortality rate and is associated with older age, underlying diseases such as diabetes, and medical procedures (such as patients who were infected in a hospital setting while undergoing an operation for other indications). Although there have been several studies describing clinical features and characteristic radiographic findings (mainly chest CT scans), limited pathologic studies have been conducted on the basis of autopsies or biopsies. Some of the reasons for the lack of autopsies and biopsies include suddenness of the outbreak, vast patient volume in hospitals, shortage of health care personnel, and high rate of transmission, which makes invasive diagnostic procedures less of a clinical priority. Even so, information regarding the lung pathology and histology of subjects who have died of COVID-19 complication has been growing.

Pathological findings in the lungs of early stage COVID-19 patients include edema, proteinaceous exudate, focal reactive hyperplasia of pneumocytes with patchy inflammatory cellular infiltration, and multinucleated giant cells; typically, hyaline membranes were not prominent. Biopsies from the lungs of later stage COVID-19 subjects exhibit one or more of desquamation of pneumocytes and hyaline membrane formation indicative of ARDS; pulmonary edema with hyaline membrane formation, suggestive of early-phase ARDS; interstitial mononuclear inflammatory infiltrates dominated by lymphocytes; multinucleate syncytial cells with atypical enlarged pneumocytes characterized by large nuclei, amphophilic granular cytoplasm, prominent nucleoli in the intra-alveolar spaces, showing viral cytopathic-like changes. Histological characteristics may include bilateral diffuse alveolar damage with cellular fibromyxoid exudates. (See e.g., Tian, et al, *Journal of Thoracic Oncology*, vol. 15 no. 5: 700-704, 28 Feb. 2020; Xu, et al., *The Lancet*, at www.thelancet.com/respiratory, vol. 8; 420-422, April 2020, herein incorporated by reference).

Methods

Disclosed herein are methods of treating lung injury that comprise administering to a patient in need thereof, a pharmaceutical composition comprising vitamin D, an analog thereof, or a metabolite thereof. In some embodiments, a subject in need thereof is diagnosed with or is at risk of developing a disease or condition that injures the lung. In some embodiments, the lung injury exhibits one or more of the following characteristics: thickening and constriction of the bronchial airways (main, proximal, and/or distal airways); luminal inflammatory exudates; absence of luminal epithelial cell layers; edema; increased reactive oxygen species (ROS); inflammation; an increase in mean pulmonary pressure, and disruption of the alveolar epithelial barrier. In some embodiments, a lung injury is caused by one or more of: acute lung injury; acute respiratory distress syndrome; chronic respiratory distress syndrome, interstitial lung disease; chronic obstructive pulmonary disease (COPD); fibrosis; infection including bacterial and viral infection; asthma; allergies; inhalation of toxic substances and/or smoke; radiation exposure; smoking; cancer; and traumatic injury to the thorax/lung, such as penetrating wounds (e.g., such as with a bullet or a knife).

Thus, the methods and compositions disclosed herein are useful for reducing inflammation, reducing inflammatory exudates, enhancing epithelial tissue generation or regeneration, reducing ROS, alleviating the disruption of the alveolar epithelial barrier, and/or reducing mean pulmonary artery pressure in the lungs of a subject in need thereof. In some embodiments, the overall health of the subject is improved as ascertained by weight gain commensurate with healing from the lung injury/disease state.

In some embodiments, the methods are useful to prevent and treat pulmonary inflammation, and pulmonary and organ failure. In some embodiments, the pulmonary inflammation is caused by an infectious agent such as a coronavirus. In some embodiments, the coronavirus is SARS-CoV-2, and the subject is diagnosed with or at risk of COVID-19. In some embodiments, the subject is diagnosed with or at risk of respiratory distress syndrome.

As shown herein, given in high doses with a strategic regimen, vitamin D is an intervention that is safely tolerated by the general and at risk population. It can be formulated to be an easy-to-use dose pack. It can help prevent and treat inflammation, for example, in symptomatic COVID19 patients. In symptomatic COVID19 subjects, the progression of symptoms from fever and body aches to worsening shortness of breath and multi-organ failure is a hallmark feature of immune activation and inflammation. By correcting the immune dysregulation COVID-related symptoms and disease severity can be reduced or eliminated.

In some embodiments, the composition is administered via one or more of the following routes: orally (e.g., as a capsule, tablet, liquid, or gel), parenterally (e.g., subcutaneously, intramuscularly, or intravenously), topically (e.g., as a cream or lotion, via iontophoresis, or transdermally, e.g., via a patch), and via inhalation.

In some embodiments, the therapeutic agent is directly administered as a pressurized aerosol or nebulized formulation to the patient's lungs via inhalation. Such formulations may contain any of a variety of known aerosol propellants useful for endopulmonary and/or intranasal inhalation administration. In addition, water may be present, with or without any of a variety of cosolvents, surfactants, stabilizers (e.g., antioxidants, chelating agents, inert gases and buffers). For compositions to be administered from multiple dose containers, antimicrobial agents are typically added. Such compositions are also generally filtered and sterilized, and may be lyophilized to provide enhanced stability and to improve solubility.

In some embodiments, compositions of the present disclosure are administered to a subject in need thereof as a single dose, one time. In some embodiments, compositions of the present invention are administered to a subject multiple times, and in some embodiments, may be administered as part of a regimen (e.g., multiple administrations over a period of time). For example, a regimen may comprise one or more doses administered to a subject in need thereof daily, weekly, bi-weekly, or monthly. In some embodiments, a regimen comprises multiple administrations over the course of one week; two weeks; three weeks; four weeks; five weeks; or six weeks. In some embodiments, a regimen comprises multiple administrations over the course of one month; two months; three months; four months; or five months. In some embodiments, a regimen comprises multiple administrations over the course of a year. In some embodiments, a regimen comprises administration once per week; administration once every other day; or administration once per day. In some embodiments, the regimen provides for an initial dose, followed by one dose per week for about 3 to about 12 weeks, or for about 4 weeks, for about 5 weeks, about 6 weeks, about 7 weeks, about 8 weeks, about 9 weeks, about 10 weeks, or about 11 weeks. In some embodiments, a regimen includes one or more initial doses, followed by weekly, bi-weekly, or monthly doses. For example, a regimen may include one or more initial doses over the course of 1 day, 2 days, 3 days, 4 days or 5 days, followed by one dose every day, every other day, or once per week for up to 1 to about 12 weeks, or one dose per month for up to about 4 months. In some embodiments, a regimen includes one dose every other day for about 1 to about 4 weeks, or one dose every day for about 3 days to about 1 week. In some embodiments, a dosage regimen comprises an initial dose, followed by one dose per week for 3 weeks, 4 weeks, 5 weeks or 6 weeks.

As described previously, dosage amount will vary depending on the condition, size, age, weight, etc. of the subject, as well as on the intended route of administration. With respect to oral administration, in some embodiments, a subject is administered one or more doses of vitamin D, an analog thereof, or a metabolite thereof, comprising for a 70 kg human subject, between about 100,000 to about 500,000 IU per dose, between about 150,000 IU to about 250,000 IU per dose, or about 200,000 IU per dose. In some embodiments, a subject is administered one or more doses of vitamin D, an analog thereof, or a metabolite thereof, for a 70 kg human subject, between about 1000 IU to about 100,000 IU per dose, between about, between about 2500 to about 75,000, between about 5000 to about 50,000 IU, between about 10,000 to about 30,000 IU.

In some embodiments, the dosage is tapered over time. By way of example, but not by way of limitation, in some embodiments, a first dose is provided at a highest dosage at Time 1 (T1), a second dose is provided at a second highest dosage at T2, a third dose is provided at a third highest dose at T3 . . . and a lowest dose is provided at Tx. In some embodiments, the timing between dosages is 2 days, 3 days, 4 days 5 days, 6 days, 7 days, or one week. In some embodiments, two consecutive doses may be the same, with the next dose being decreased (e.g., dose 3 and 4 may be the same, but dose 5 is lower than dose 4). An exemplary, non-limiting dosage scheme is 200,000 IU at day 1 of illness; 100,000 IU at day 5 of illness; 50,000 IU at day 10 of illness; and 50,000 IU at day 15 of illness.

In some embodiments, the method comprises administering to a subject in need thereof, a composition comprising vitamin $D_3$, wherein the composition is formulated for oral administration and comprises between about 100,000 to about 300,000 IU per dose, as calculated for a 70 kg human. In some embodiments, the composition comprises about 200,000 IU per dose. In some embodiments, the dosage regimen comprises an initial dose, followed by one dose per week for about 3 weeks, about 4 weeks, or about 5 weeks. In some embodiments, the dosage is tapered over time.

In some embodiments, the method comprises administering to a subject in need thereof, a composition comprising vitamin $D_3$, and a diuretic, such as spironolactone. In some embodiments, the composition is formulated for oral administration and comprises, for vitamin D, between about 100,000 to about 300,000 IU per dose, as calculated for a 70 kg human. In some embodiments, the composition comprises about 200,000 IU per dose of vitamin D. In some embodiments, the composition comprises between about 50-400 mg of diuretic (e.g., spironolactone). In some embodiments, the composition comprises about 50, about 75, about 100, about 150, about 200, about 400, or about 400 mg of diuretic. In some embodiments, the composition comprises 0.312 to 19.6 weight percent of vitamin D, an analog thereof, or a metabolite thereof, and at least 80.4 to 96.9 weight percent of a diuretic. In some embodiments, the composition comprises 0.312 to 19.6 weight percent of vitamin D, an analog thereof, or a metabolite thereof, and at least 80.4 to 96.9 weight percent of a diuretic based on the total weight of active pharmaceutical ingredients only. In some embodiments, the dosage regimen comprises an initial dose, followed by one dose per week for about 3 weeks, about 4 weeks, or about 5 weeks.

The methods and compositions disclosed herein result in improvements to the condition of the treated subject as compared to an untreated subject with the same or similar symptoms, and/or with the same or similar disease or condition. Improvements include, but are not limited to reducing pulmonary inflammation, reducing pulmonary inflammatory exudates, enhancing pulmonary epithelial tissue generation or regeneration, reducing pulmonary ROS, alleviating the disruption of the alveolar epithelial barrier, and/or reducing mean pulmonary artery pressure in the lungs of a subject in need thereof. In some embodiments, the overall health of the subject is improved as ascertained by one or more of weight gain commensurate with healing from the lung injury/disease state, easier breathing, less coughing, increased blood oxygen level, and reduced fever. In some embodiments, improvement in the condition of a treated subject is noted within about 24 hours after an initial administration of a composition as disclosed herein, as compared to the condition of an untreated control subject. In some embodiments, an improvement is noted within about 2 days, within about 3 days, within about 4 days or within about a week after an initial administration. In some embodiments, improvement is noted after about 1 week, after about 2 weeks, after about 3 weeks or after about 4 weeks, after an initial administration. In some embodiments, one or more improvements to a treated subject occur sooner than in an untreated subject with the same or similar symptoms, disease, or condition.

ILLUSTRATIVE EMBODIMENTS

Embodiment 1. A method for treating an injury in the lungs of a subject in need thereof, comprising: administering an effective amount of a composition comprising vitamin D, an analog thereof, or a metabolite thereof.

Embodiment 2. The method of embodiment 1, wherein the injury is characterized by one or more of: thickening and constriction of the bronchial airways (main, proximal, and/or distal airways); luminal inflammatory exudates; absence of luminal epithelial cell layers; edema; increased reactive oxygen species (ROS); inflammation; and disruption of the alveolar epithelial barrier.

Embodiment 3. The method of embodiment 1 or 2, wherein the lung injury is caused by one or more of: acute lung injury; acute respiratory distress syndrome; chronic respiratory distress syndrome, interstitial lung disease; chronic obstructive pulmonary disease (COPD); fibrosis; infection including bacterial and viral infection; asthma; allergies; inhalation of toxic substances and/or smoke; radiation exposure; smoking; cancer; and traumatic injury to the thorax/lung, such as penetrating wounds.

Embodiment 4. The method of embodiment 1, wherein the injury is characterized by inflammation.

Embodiment 5. The method of embodiment 1, wherein the injury is characterized by one or more of thickening of bronchial airways, constriction of bronchial airways, luminal inflammatory exudates, and loss of luminal epithelial layer.

Embodiment 6. The method of embodiment 1, wherein the injury is caused by an infection.

Embodiment 7. The method of embodiment 6, wherein the infection comprises a viral infection.

Embodiment 8. The method of embodiment 7, wherein the viral infection comprises a coronavirus infection.

Embodiment 9. The method of embodiment 8, wherein the coronavirus infection comprises SARS-CoV-2.

Embodiment 10. The method of embodiment 1, wherein the subject is diagnosed with or at risk of having COVID-19.

Embodiment 11. The method of any one of the preceding embodiments, wherein the composition comprises one or more of vitamin D, and 1,25-dihydroxyvitamin D.

Embodiment 12. The method of any one of the preceding embodiments, wherein the composition comprises vitamin D3.

Embodiment 13. The method of any one of the preceding embodiments, wherein the composition comprises calcitriol.

Embodiment 14. The method of any one of the preceding embodiments, wherein the composition is administered orally.

Embodiment 15. The method of any one of the preceding embodiments, wherein the compositions is administered by inhalation.

Embodiment 16. The method of any one of the preceding embodiments, wherein the composition is administered in a regimen comprising multiple administrations.

Embodiment 17. The method of embodiment 16, wherein the regimen comprises multiple administrations over the course of one week; two weeks; three weeks; four weeks; five weeks; or six weeks.

Embodiment 18. The method of embodiment 16, wherein the regimen comprises multiple administrations over the course of one month; two months; three months; four months; or five months.

Embodiment 19. The method of embodiment 16, wherein the regimen comprises multiple administrations over the course of a year.

Embodiment 20. The method of any one of embodiments 16-19, wherein the regimen comprises administering an initial dose, followed by administration of another dose once per week for about 3 weeks to about 12 weeks.

Embodiment 21. The method of any one of embodiments 16-19, wherein the regimen comprises administration of a single dose once every other day for about 1 week to about 4 weeks.

Embodiment 22. The method of any one of embodiments 16-19, wherein the regimen comprises administration of a single dose once per day for about 3 days to about 7 days.

Embodiment 23. The method of any one of the preceding embodiments, wherein the composition comprises between about 100,000 IU to about 300,000 IU per dose of vitamin D, an analog thereof, or a metabolite thereof.

Embodiment 24. The method of any one of the preceding embodiments, wherein the composition comprises between about 150,000 IU to about 250,000 IU per dose of vitamin D, an analog thereof, or a metabolite thereof.

Embodiment 25. The method of any one of the preceding embodiments, wherein the composition comprises between about 200,000 IU per dose of vitamin D, an analog thereof, or to metabolite thereof.

Embodiment 26. The method of embodiment 1, wherein the composition comprises, in addition to vitamin D, an analog thereof or a metabolite thereof, one or more additional active agents.

Embodiment 27. The method of embodiment 22, wherein the additional active agent comprises one or more of an anti-inflammatory agent, a bronchodilator, an anti-viral agent, an antibiotic, and a diuretic.

Embodiment 28. The method of embodiment 27, wherein the additional active agent comprise a diuretic; and wherein the diuretic comprises spironolactone.

EXAMPLES

The following examples are illustrative and should not be interpreted to limit the scope of the claimed subject matter.

Example 1: Vitamin D Alleviates Inflammation and Promotes Tissue Repair in Injured Lungs The purpose of the study was to determine the efficacy of oral vitamin D3 (20,000 IU/kg in rats equals the human equivalent dose of 2857 I.U./kg) and optimal dosing regimen following severe lung injury in an inhalation model. Outcomes included survival, maintenance of weight, clinical severity, and lung epithelial damage.

Induction of lung injury: Using a vapor inhalation model, twenty-four adult rats were exposed to sulfur mustard (SM) 1.0 mg/kg.

Study protocol:
Study duration: 25 days
Study Groups Design:
  Group 1: Vitamin D3—4 hrs post exposure n=8 (1 treatment)
  Group 2: Vitamin D3—4 hrs post exposure, 3 d, 7 d n=8 (2 treatments)
  Group 3: Vitamin D3—4 hrs post exposure, 7 d, 14 d, 21 d n=8 (4 treatments)
  Group 4: Placebo—4 hrs post exposure, 7 d, 14 d, 21 d n=6 (placebo)
Drug studied (dose, route, interval): Vitamin $D_3$ (20,000 IU/kg, PO) in olive oil was calculated per each animal's weight (~1 ml). Vitamin $D_3$ dose calculation: Based on human trials, we modelled oral vitamin $D_3$ treatment for rats based on human dosing of 200,000 I.U. per dose in a 70 kg person. The established Human Equivalent Dose (HED) to rat is 1:6.2, thus resulting in a calculated dose of 20,000 IU/kg/dose in rats. Olive oil placebo, volume calculated per each animal's weight (~1 ml). Intervals are listed above in Study Group Design.

Drug Source: Nivagen Pharmaceuticals
Rat Strain/Vendor: Charles River Sprague Dawley Rats
Rat Weight Range (start of study): 250-277 g
Supplemental Care Administered:
  Daily DietGel Recovery starting at day 1
  Saline injections (subQ) when weight loss greater than 20% from peak weight
Euthanasia Criteria:
  Animal loses 30% or more of peak body weight
  Animal has average pOx<70% AND clinical score of 7 or greater
Animal Exclusions with Reasons: 2
  SM223b—(Group 3)—Reason: Ear trauma—necrotic ear wound—euthanized on day #19
  SM245b—(Group 2)—Reason: Esophageal perforation—Found Dead on day #1
Study Deviations: None
Study Endpoints (List):
  Survival, pulse ox, heart rate, clinical score, Weight, respiratory rate
  Arterial blood gas, Complete Blood Count, Clinical chemistry
  Cardiac catheterization at End of Study
  Echocardiogram once weekly (pre, 7 d, 14 d, 21 d)
  Lung function (Flexivent) at end of study
  Lung histology
Statistics: ANOVA, non-parametric, mean; unpaired t-test (if applicable).
Results At 25 days, the rats were sacrificed and lung tissue was analyzed to determine the extent of tissue damage in the untreated controls, and to determine vitamin D effects in the treated groups. (See FIGS. 3-6). A summary of findings is presented below.

4-dose treatment regimen (given 4 hrs, then 7, 14, 21 days post exposure)
  best survival benefit (100% vs. 67% in SM controls at 25 days)
  greatest improvement in weight gain (21% vs. 8% in SM controls at 25 days)
  mean Pulmonary Artery Pressures (mPAP) decrease was best in this treatment group, decreasing to normal at 25 days (18.3 vs. 26.4 mmHg in SM controls).
  total airways resistance was trending towards a decrease in this group, but total compliance was unchanged from SM controls.
  histology shows the improvement in airway epithelial layer presence, with continuous layer seen in both proximal and distal airways, with minimal inflammation and exudate presence within the lumen
3-dose treatment regimen (given 4 hrs, then 3, 7 days post exposure)
  2nd highest survival benefit (85% vs. 67% in SM controls at 25 days)
  initial improvement in weight gain over the first 12 days was seen, similar to 4-dose treatment group, but then this benefit was lost between 13-25 days (2% vs 8% in SM controls at 25 days)
  mPAP decreased at 25 days over controls (20.9 vs. 26.4 mmHg in controls)
  total airways resistance was trending towards a decrease in this group, but total compliance was unchanged from SM controls histology shows some discontinuous airway epithelial layer presence in both proximal and distal airways, with moderate inflammation and moderate exudate present within the lumen 1-dose treatment regimen (given 4 hrs post exposure)
no improvement in survival over control (63% vs. 67% in SM controls)
initial improvement in weight gain over the first 8 days, similar to 4-dose and 3-dose treatment groups, but benefit was lost between 9-25 days, with significant deaths resulting in data drop out
mPAP decreased at 25 days over controls (20.0 vs. 26.4 mmHg in SM controls)
no improvement in airways resistance or compliance
histology shows no improvement in airway wall over control, with a complete absence of airway epithelium, severe wall thickening and inflammation, as well as severe inflammatory exudate impaction of airways.

As shown in FIGS. 5 and 6, a repeated oral vitamin D3 dosing regimen after lung injury improved the airway epithelial barrier and wall thickness, and greatly decreased luminal inflammatory exudates.

FIG. 5A shows a 4× magnification the distal left lung section of an untreated (placebo group) 25 days after exposure to sulfur mustard (SM). Severe thickening and constriction of the main bronchial airway (long arrow), with severe luminal inflammatory exudate, and an absence of a luminal epithelial cell layer (see insert, short arrow) is observed. FIG. 6, left panels, shows a 20× magnification of the proximal large airway and distal medium sized airway of untreated (placebo group) rats 25 days after SM exposure. Again, severe wall thickening and severe luminal inflammatory exudate is seen in both proximal and distal airways, and a complete absence of a luminal epithelial cell layer is observed.

In contrast, FIG. 5B shows the distal left lung of a 4-dose vitamin D treated rat, 25 days after exposure to SM. Minimal thickening of the main bronchial airway (long arrow), with scant to no luminal exudates were observed. Also, a continuous luminal epithelial cell layer was observed (see insert, short arrow). FIG. 6, right panels, show the distal and proximal airways in 4-dose vitamin D treated rats. An intact airway epithelial barrier, decreased wall thickening, and greatly decreased inflammatory exudates were observed.

Example 2—Prophetic: High Dose Vitamin D Regimen Will be Useful to Treat COVID-19 Symptoms A 60 year old male patient is admitted to the local emergency room and presents with symptoms characteristic of COVID-19, including a cough, fever, chills, muscle aches, difficulty breathing, and low blood oxygen level. The patient is tested and found to be positive for SARS-CoV-2 infection, and COVID-19 is confirmed. The patient is immediately given supplemental oxygen and is treated with 200,000 IU oral vitamin D3. Oxygen support is continued, and fever-reducing measures are provided. The patient is monitored, and vitals, such as blood oxygen levels and respirations, are recorded upon intake and during hospitalization and treatment. Chest CTs are also recorded. The patient is given additional doses of vitamin D3 (200,000 IU per doses) once per week. It is anticipated that the subject's vital signs, such as oxygen levels and respirations, will show improvement sooner than a patient that did not received vitamin D3 treatment. It is further anticipated that imaging analysis of the patient's lungs will show improvement sooner than a patient that did not receive vitamin D treatment.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

Citations to a number of patent and non-patent references may be made herein. Any cited references are incorporated by reference herein in their entireties. In the event that there is an inconsistency between a definition of a term in the specification as compared to a definition of the term in a cited reference, the term should be interpreted based on the definition in the specification.

We claim:

1. A method for treating an injury in the lungs of a subject in need thereof, the method comprising: administering, as part of a regimen, an effective amount of a composition comprising vitamin D3, wherein the regimen comprises orally administering an initial dose of the composition followed by orally administering at least three additional doses of the composition, wherein a first dose of the at least three additional doses is administered five to seven days from the initial dose, and wherein the remaining doses of the at least three additional doses is administered five to seven days apart from one another, and wherein (i) the initial dose, (ii) the at least three additional doses, or (iii) both (i) and (ii) comprise about 100,000 IU to about 500,000 IU of vitamin D3.

2. The method of claim 1, wherein the injury is characterized by one or more of: thickening and constriction of the bronchial airways (main, proximal, and/or distal airways); luminal inflammatory exudates; absence of luminal epithelial cell layers; edema; increased reactive oxygen species (ROS); inflammation; and disruption of the alveolar epithelial barrier.

3. The method of claim 1, wherein the lung injury is caused by one or more of: acute lung injury; acute respiratory distress syndrome; chronic respiratory distress syndrome, interstitial lung disease; chronic obstructive pulmonary disease (COPD); fibrosis; infection including bacterial and viral infection; asthma; allergies; inhalation of toxic substances and/or smoke; radiation exposure; smoking; cancer; and traumatic injury to the thorax/lung, such as penetrating wounds.

4. The method of claim 1, wherein the injury is characterized by inflammation.

5. The method of claim 1, wherein the injury is characterized by one or more of thickening of bronchial airways, constriction of bronchial airways, luminal inflammatory exudates, and loss of luminal epithelial layer.

6. The method of claim 1, wherein the injury is caused by a viral infection.

7. The method of claim 6, wherein the injury is caused by a SARS-CoV-2 infection.

8. The method of claim 1, wherein the composition further comprises, one or more additional active agents.

9. The method of claim 8, wherein the one or more additional active agents comprises one or more of an anti-inflammatory agent, a bronchodilator, an anti-viral agent, an antibiotic, and a diuretic.

10. The method of claim 9, wherein the one or more additional active agents comprises a diuretic; and wherein the diuretic comprises spironolactone.

11. The method of claim 1, wherein the injury in the lungs is at least partly due to inhalation of a toxic substance, and wherein the injury in the lungs is characterized by thickening of bronchial airways, luminal inflammatory exudates, and loss of luminal epithelial layer.

12. The method of claim 11, wherein after administering the at least three additional doses of the composition the treated lung exhibits improvement in one or more of bronchial airway thickness, luminal exudate, and luminal epithelia cell layer, as compared to an untreated control.

\* \* \* \* \*